United States Patent
De Godzinsky et al.

(10) Patent No.: US 9,314,217 B2
(45) Date of Patent: *Apr. 19, 2016

(54) COLLIMATOR ARRANGEMENT IN CONNECTION WITH INTRA-ORAL X-RAY IMAGING

(75) Inventors: Christian De Godzinsky, Vamtaa (FI); Kustaa Nyholm, Siuntio (FI)

(73) Assignee: PLANMECA OY, Helsinki (FI)

( * ) Notice: Subject to any disclaimer, the term of this patent is extended or adjusted under 35 U.S.C. 154(b) by 131 days.

This patent is subject to a terminal disclaimer.

(21) Appl. No.: 14/006,411

(22) PCT Filed: Mar. 21, 2012

(86) PCT No.: PCT/FI2012/050286
§ 371 (c)(1),
(2), (4) Date: Sep. 20, 2013

(87) PCT Pub. No.: WO2012/127115
PCT Pub. Date: Sep. 27, 2012

(65) Prior Publication Data
US 2014/0010350 A1     Jan. 9, 2014

(30) Foreign Application Priority Data
Mar. 21, 2011   (FI) .................................... 20110105

(51) Int. Cl.
G21K 1/04    (2006.01)
A61B 6/14    (2006.01)
A61B 6/06    (2006.01)
A61B 6/00    (2006.01)
A61B 17/00   (2006.01)

(52) U.S. Cl.
CPC . *A61B 6/145* (2013.01); *A61B 6/06* (2013.01); *A61B 6/14* (2013.01); *A61B 6/587* (2013.01); *A61B 6/4452* (2013.01); *A61B 2017/00867* (2013.01)

(58) Field of Classification Search
CPC ........... G01N 23/04; G21K 1/02; G21K 1/04; A61B 6/06; A61B 6/14; A61B 6/547; A61B 6/587
USPC ............................ 378/62, 147, 150, 151, 205
See application file for complete search history.

(56) References Cited

U.S. PATENT DOCUMENTS

| | | |
|---|---|---|
| 4,223,228 A | 9/1980 | Kaplan |
| 5,463,669 A * | 10/1995 | Kaplan .................. 378/205 |
| 2001/0012330 A1 | 8/2001 | Ogura et al. |
| 2014/0010349 A1 * | 1/2014 | De Godzinsky et al. ....... 378/62 |

\* cited by examiner

*Primary Examiner* — Jurie Yun
(74) *Attorney, Agent, or Firm* — Fay Sharpe LLP

(57) ABSTRACT

The invention relates to an intra-oral x-ray imaging arrangement which includes as separate structures, first, a radiation source (4) having a collimator structure (4', 40) limiting an x-ray beam for producing the beam used in imaging and for aiming it to the object to be imaged, secondly, an imaging sensor (30) arranged positionable within a patient's mouth (30), and a control system of the imaging arrangement. The collimator structure (4', 40) is implemented as a structure (40) which enables adjusting a collimator opening limited by the collimator for at least one of the following: its size, its shape, its location, its position.

24 Claims, 4 Drawing Sheets

50

COLLIMATOR ARRANGEMENT IN CONNECTION WITH INTRA-ORAL X-RAY IMAGING

TECHNICAL FIELD

The present invention relates especially to collimating an x-ray beam in connection with mutual positioning of an intra-oral x-ray device and an intra-oral x-ray sensor in connection with an imaging event.

BACKGROUND OF INVENTION

Dental intra-oral x-ray images are taken by using x-ray examination devices which typically include a multi-jointed arm construction and an x-ray source placed inside a housing. Typically, an elongated collimator limiting an x-ray beam has been attached or arranged to be attached to the housing. The imaging process includes placing the x-ray device in the proximity of the object area to be imaged and aiming the x-ray beam such that it will hit the sensor in a correct orientation and at a desired angle. Typically, one aims for arranging the beam perpendicular with respect to a film or some other detector of image information used in the imaging.

Problems related to aiming and orientating the beam as well and to the beam not being inclined or turned with respect to an image-data receiving means are generally known by dental professionals. Thus, different aiming arrangements have been developed to facilitate correct positioning of the x-ray source with respect to the sensor. One approach according to prior art is to attach the x-ray source and the image-data receiving means, such as a film, a phosphorous imaging plate, a CCD sensor or some other digital sensor, physically to each other for the duration of an exposure. Some prior-art systems and assemblies utilising this approach are presented in patent specifications U.S. Pat. No. 6,343,875 B1, U.S. Pat. No. 5,632,779 A, U.S. Pat. No. 4,507,798 A and U.S. Pat. No. 4,554,676 A.

However, many dental professionals find these systems, where the sensor placed within the patient's mouth should be physically connected to the x-ray device, difficult to use in practice. A reason for this is, first, that if all connections of the assembly are made before positioning the sensor in the mouth, it has proven difficult to aim the entire relatively heavy construction including the x-ray tube and its anti construction into a precisely correct position desired at a given instance. Secondly, if the sensor is first placed in the correct position in the mouth, it has proven difficult to e.g. attach an aiming shaft to assemble the construction such that the attaching process would not cause the sensor to move or cause discomfort to the patient.

In the field, one has also been contemplating arrangements in which information on the position of the imaging sensor would be obtained by means of sensors detecting the position, belonging to the imaging arrangement. Inter alia, a magnetic field has been disclosed to be utilised in positioning, but there have been no e.g. such arrangements based on measurement signals on the market which would be able to unambiguously determine the mutual spatial location and orientation of the imaging sensor and the radiation source, let alone to adjust and aim the beam accurately to the sensor based on such information. Again, evidently the only procedure on the market to adjust the size or shape of the beam generated by the intra-oral x-ray device that one could consider being based on technical arrangements of the apparatus itself has been manual replacement of collimator plates, collimator tubes or equivalent arranged into connection with the radiation source.

SUMMARY OF INVENTION

The object of the present invention and its preferable embodiments is to provide novel arrangements for collimating a beam in connection with intra-oral x-ray imaging, especially in connection with an arrangement which includes means to detect the position of a sensor, particularly with respect to the beam generated by an x-ray source to be used in the imaging.

Essential characteristics of the invention and its preferable embodiments are presented in the enclosed patent claims. In preferable embodiments of the invention, the true mutual positioning of the intra-oral x-ray source and the imaging sensor can be monitored even real-time, based on certain measurement signals and without having to visually estimate their mutual position, whereby collimation of the beam to the sensor can be arranged motorised or otherwise operable by electric power such that there is no need for the user to attend to the collimation but it is automatically taken care of by the imaging arrangement.

In the preferable embodiments of the invention, means are arranged into connection with both the intra-oral imaging sensor and the radiation source to measure their spatial position and, further, means to the control system of the arrangement to generate information based on said measurement signals on the mutual positioning of the imaging sensor and the radiation source. In one preferable embodiment of the invention, a three-axis magnetic sensor as well as a three-axis acceleration sensor are arranged into connection with both the imaging sensor and the radiation source, based on measurement signals obtained from which, the control system of the arrangement is configured to define both the mutual tilt angle of the imaging sensor and the radiation source and their mutual spatial orientation.

Thus, in one preferable embodiment of the invention, a three-axis magnetic sensor is arranged, on the one hand, into connection with the imaging sensor, preferably substantially at the centre point of its imaging area behind the sensor, on the other hand, into connection with the x-ray source, preferably into proximity of the collimator structure of the x-ray source. In one preferable embodiment of the invention, into connection with the imaging sensor and the radiation source is further arranged a three-axis acceleration sensor. Then, it is possible to calculate based on measurement signals obtained from the sensors, first, the mutual tilt of the imaging sensor and the x-ray source and, second, rotation in a three-dimensional set of coordinates.

The use of the abovementioned acceleration and magnetic sensors is based on an idea to utilise measurement information on the earth's magnetic and gravitational fields. In a preferable embodiment of the invention, a known magnetic field generated by the arrangement itself is included in this system. This field can then be utilised to solve, based on measurement signals generated to be used in the arrangement, a directional vector defining the mutual location of the imaging sensor and the radiation source.

Thus, preferable embodiments of the invention also enable finding out the location of the centre of the imaging area of the imaging sensor in relation to the centre ray of the beam, as well as the distance between the imaging sensor and the radiation source, and so also between the sensor and a collimator preferably arranged to the radiation source. These data are needed especially when one wishes the control system of the imaging arrangement to be able either automatically or as guided to set the mutual positioning of the imaging sensor and the radiation source such that the sensor is completely within the beam, the centre ray of the beam hits the centre of the imaging area of the sensor, and the x-ray beam is limited substantially precisely according to the imaging area of the imaging sensor.

Consequently, in one preferable embodiment of the invention, into connection with the collimator structure of the radiation source is preferably arranged a thin ring-like coil, which is arranged to generate a controlled direct-current magnetic field. Then, in a way described in more detail below, it is possible to solve based on measurement signals obtained from the three-axis magnetic sensor arranged into connection with the imaging sensor at which distance and in which direction the imaging sensor is located with respect to the radiation source (i.e. with respect to said coil).

In one preferable embodiment of the invention, means are arranged to the control system of the arrangement to prevent exposure when based on the measurement signals generated by the system the imaging sensor is not in the beam or close enough to the radiation source. Correspondingly, the arrangement can be set to automatically arm to a standby mode of exposure when the imaging sensor is detected to be located within the area of the x-ray beam. The arrangement can even be configured with an operation mode to shoot an image independently in a situation when it recognizes that predetermined location and orientation criteria are met. Then in one embodiment of the invention, a trigger, which is used in normal operation to give a starting signal for the exposure, can be arranged to operate as a safety device which gives a signal for allowing automatic triggering or for switching the automatic exposure mode on and off.

By means of preferable embodiments to be described in more detail below, it is possible to automatically detect location of the imaging sensor with respect to the radiation source concerning the tilt angle, rotation and distance as well as the location of the centre of the imaging area of the sensor in relation to the centre ray of the x-ray beam. This enables guiding the user e.g. on a display or some other means of transmitting information to set the mutual position of the radiation source and the sensor as desired.

Next, principles and preferable embodiments of the present invention will be described in more detail by means of examples. The embodiments in question are presented as examples and are not intended to show all the possibly conceivable different configurations and modifications of the invention but the characteristic features of the invention are defined in the enclosed claims.

DETAILED DESCRIPTION OF INVENTION

Figure 1:
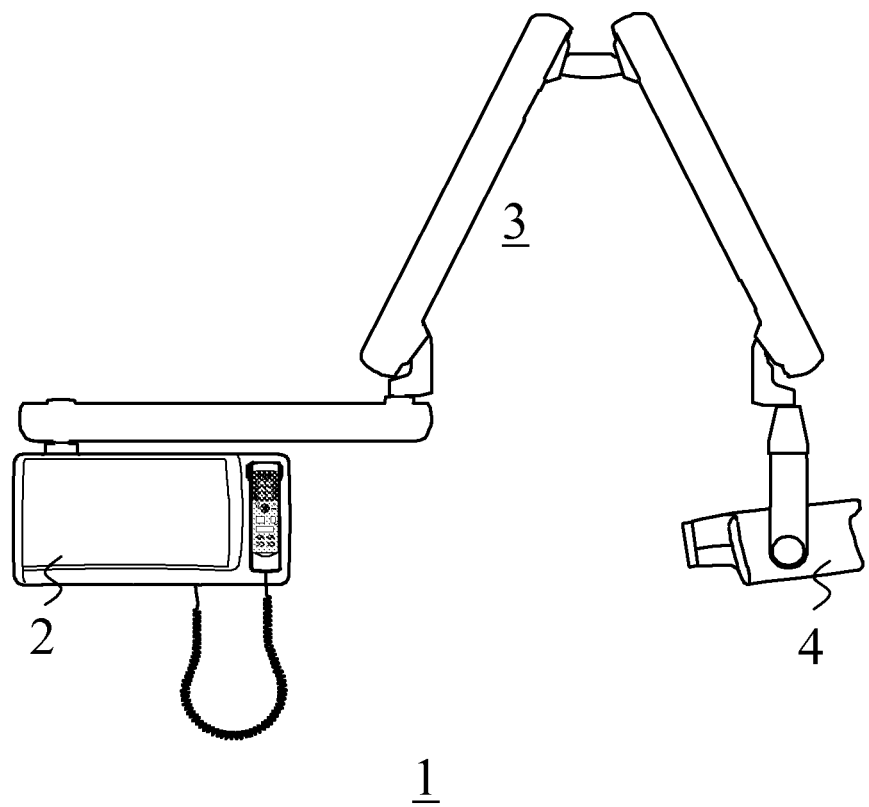
FIGS. 1, 2*a* and 2*b* show one typical intra-oral x-ray device.
Figure 2:
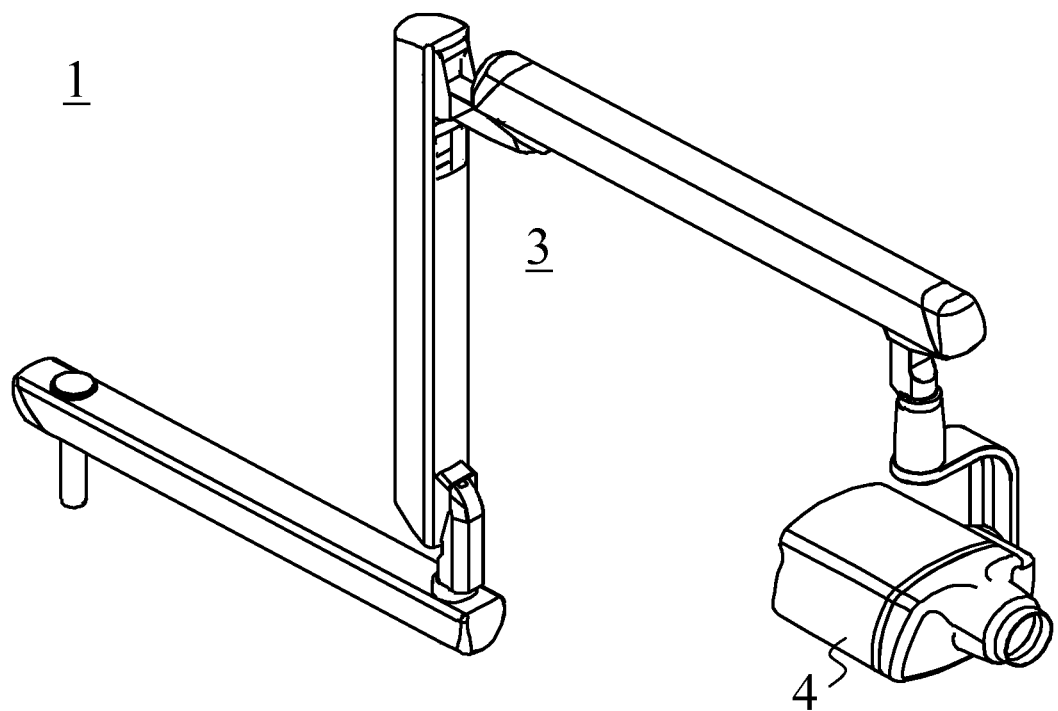
Figure 2:
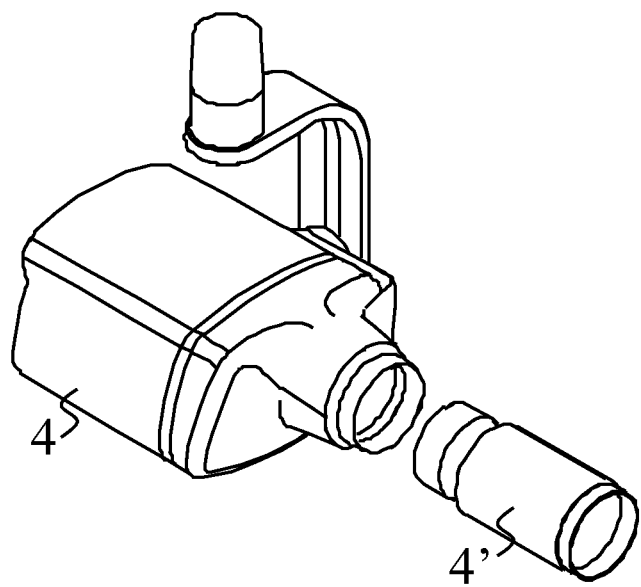

FIGS. 1, 2*a* and 2*b* show a typical intra-oral x-ray device (1) which includes a control panel (2), a jointed arm construction (3) and an x-ray source (4). FIG. 2*b* additionally shows an elongated collimator tube (4') which can be attached to a housing of the x-ray source (4) for limiting the x-ray beam more precisely and thus minimising the radiation dose received by a patient.

Figure 3:
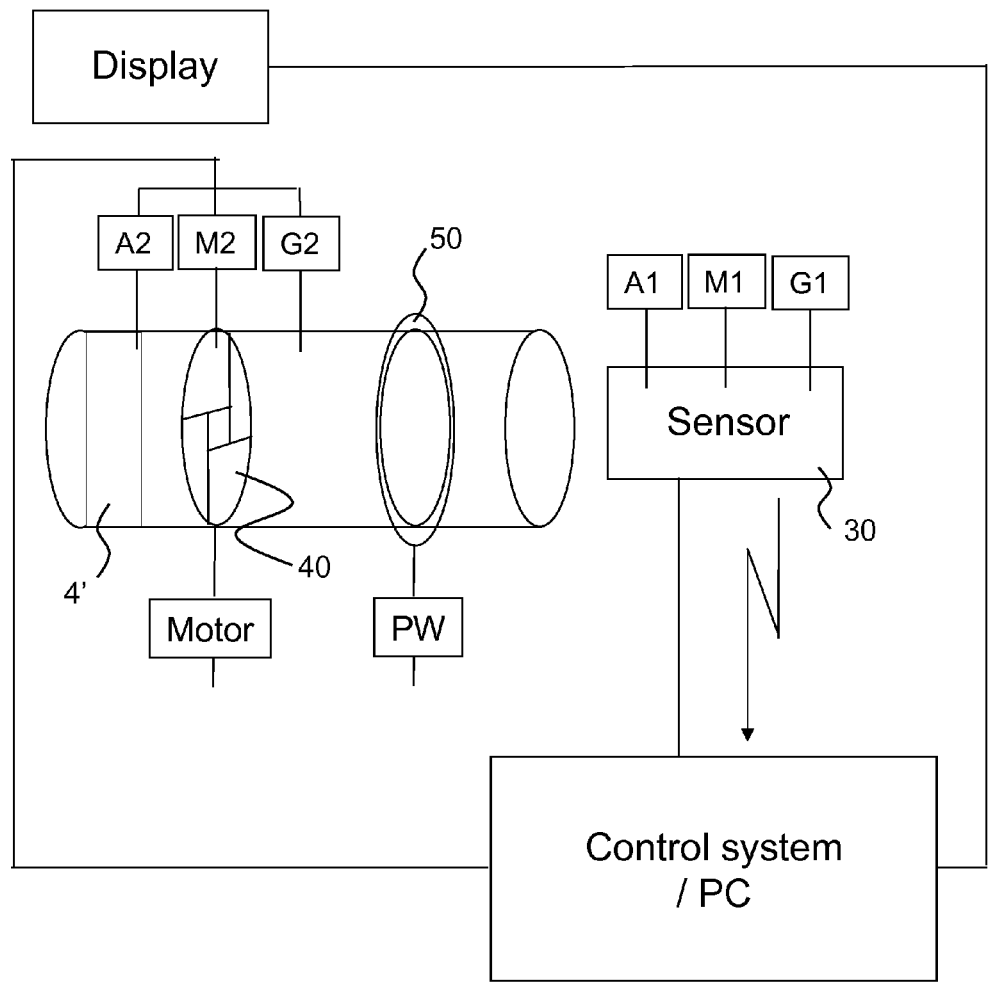
FIG. 3 shows basic components of one arrangement according to one preferable embodiment of the invention.

FIG. 3 shows basic components of an arrangement according to one preferable embodiment of the invention. The arrangement includes, first, a coil (50) arranged into proximity of a motorised collimator plate structure (40) located in connection with the collimator tube (4') of the radiation source. The collimator plate structure (40) in question is arranged to form an adjustable opening and so to limit radiation generated by the radiation source to a beam as desired. Preferably, this structure is positioned at a distance from that opening of the collimator tube from which the beam generated by the radiation source is aimed at the object. The coil (50) is preferably connected to a direct-current supply (PW) which supplies current as pulsed. Preferably, the coil (50) is arranged into connection with the collimator tube (4') cocentrically with the collimator plate structure (40). Into connection with the radiation source, preferably into connection with said collimator plate structure (40), are also arranged a three-axis gyro sensor (G2) and three-axis acceleration and magnetic sensors (A2, M2). Into connection with the radiation source or in some other suitable place is also arranged a display (D).

Correspondingly, into connection with the imaging sensor (30) are arranged a three-axis gyro sensor (G1) and three-axis acceleration and magnetic sensors (A1, M1). Of these, preferably the magnetic sensor (M1) is arranged substantially at the centre of the imaging area of the sensor, on the side of the sensor opposite to where a pixel matrix of the sensor detecting radiation is located. The sensors pertaining to the arrangement according to FIG. 3 are arranged into functional connection with a control system of the arrangement, which may be located e.g. in a customary PC but also somewhere else, e.g. at least for some of its parts in connection with the radiation source (4). The control system is configured to receive measurement signals from the sensors and, based on them, to generate information related to the position and location of the imaging sensor (30) and the radiation source (4) pertaining to the imaging arrangement. Furthermore, the control system either controls the pulsing of the power supply (PW) of the coil (50) or at least information on the pulsing in question is conveyed or has been conveyed to it.

It should be emphasised here that the arrangement according to FIG. 3 forms a combination of several preferable embodiments of the invention, that is, the basic idea of the invention can also be realised with other kinds of arrangements than the one shown in FIG. 3 and all practical embodiments of the invention do not necessarily employ all components or arrangements shown in FIG. 3.

Next, the purpose and operation of different components and partial arrangements of the arrangement according to FIG. 3 will be examined in more detail.

The acceleration and magnetic sensors (A1, A2, M1, M2) are arranged into functional connection with the control system, which includes means to define based on measurement signals obtained from the those sensors the orientation of the sensor (30) and the radiation source (4) with respect to the earth's gravitational and magnetic fields. Furthermore, the control system includes means to determine the location of the magnetic sensor (M1) arranged to the sensor (30) with respect to the magnetic field generated by the coil (50) arranged into connection with the radiation source (4).

Information on the mutual orientation of the sensor (30) and the radiation source (4) essentially relating to realizing the invention can be found out with a multi-phase calculation which is based on several measurement signals. Employable in the invention are, for instance, three-axis magnetic and acceleration sensors, i.e. sensors which are arranged with three individual sensor units arranged at solid angles different from each other. Such sensors are also available commercially, e.g. Honeywell's GMR magnetic sensor HMC5843 and Kionix's acceleration sensor KXPS5-2050. Such sensors are able to measure in addition to the intensity of a magnetic or gravitational field also the direction of a field vector at the measuring point. Then, information acquisition of the arrangement according to FIG. 3 can include calculation of a cross product of the directional vectors measured by the acceleration and magnetic sensors (A1, M1; A2, M2. This cross product vector is thus at the right angles with both the gravitational field and the earth's magnetic field. When a second cross product is further formed between the first-formed cross product and a measured acceleration vector, these two cross products and the acceleration vector form axes of an orthogonal set of coordinates the orientation of which with respect to the earth's magnetic field and gravitational field is known. When the control system of the arrangement knows how the acceleration and magnetic sensors (A1, A2, M1, M2) are positioned into connection with the radiation source (4) and the sensor (30), it is further known how they would be positioned in the set of coordinates as of above, whereby it is also possible to determine the mutual spatial orientation of the radiation source and the sensor. Thus, one is able to find out e.g. the tilt between a surface comprising the imaging area of the sensor (30) and a surface comprising the collimator opening of the collimator structure (40) located at the radiation source (4), and also the rotation of the sensor (30) with respect to the beam generated by the radiation source (1).

In connection with intra-oral x-ray imaging, there typically is less than the distance of dozens of centimeters between the sensor (30) and the radiation source (4) during exposure. Hence, determining the mutual position as above is based on an assumption that the earth's magnetic field is substantially the same at the point of both the sensor (30) and the radiation source (4) and that it is unlikely that any disturbances, even local ones, in the earth's magnetic field can substantially change this state of affairs. Furthermore, it is substantial for the functioning of the arrangement that such measurement signals are used which have been obtained in a situation where the sensor (30) and the radiation source (4) are in non-accelerated motion, i.e. essentially stationary, in practise.

In practice, signals obtained from sensors of the above type (A1, A2, M1, M2) have to be subjected to various filterings, e.g. low-pass filtering. Due to this, there may be slight delays in the information acquisition of the kind above. On the other hand, the measurement signal obtained from the acceleration sensor (A1, A2) cannot be effectively utilised in situations where the sensor is in an accelerating motion.

A gyro sensor (G1, G2) is a sensor the integral of the measurement signal obtained from which reveals the position of the sensor with respect to a reference position of the sensor used at a given instance. An example of such a sensor is manufacturer InveSense's product ITG-3200. The measurement signal obtained from such a sensor is not, however, constant with respect to time but there is some drift. Thus, using solely gyro sensors (G1, G2) is not necessarily an optimal solution for the practical operation of the present arrangement, but with the help of a gyro sensor or gyro sensors the operation of the above arrangement based on the magnetic and acceleration sensors (A1, A2, M1, M2) can be speeded up. In such an embodiment of the invention, the arrangement can be implemented such that the integrated signal of the gyro sensor (G1, G2) is corrected as a function of time e.g. by using Kalman filtering, e.g. by correcting said integrated signal by filtered signals which are constant but slow with respect to time, obtained from the other sensors (A1, A2, M1, M2) of the arrangement.

The power supply (PW) of the coil (50) arranged into connection with the radiation source is a direct-current supply which is preferably arranged to supply current as pulsed. Then, the coil (50) generates a controllably alternating magnetic field. Preferably, the power supply is cut off on a low frequency either as controlled by the control system or such that the control system still has information on which kind of a magnetic field the coil (50) generates at each moment in time or if it generates any field at all. Preferably, this arrangement thus generates in a desired periodicity a controlled direct-current magnetic field of a desired size, preferably always of the same size and e.g. such that the field intensity is constant and its magnitude at some desired point at a distance in the range of about 5-15 cm from the coil is of the order of 0.4 G.

Figure 4:
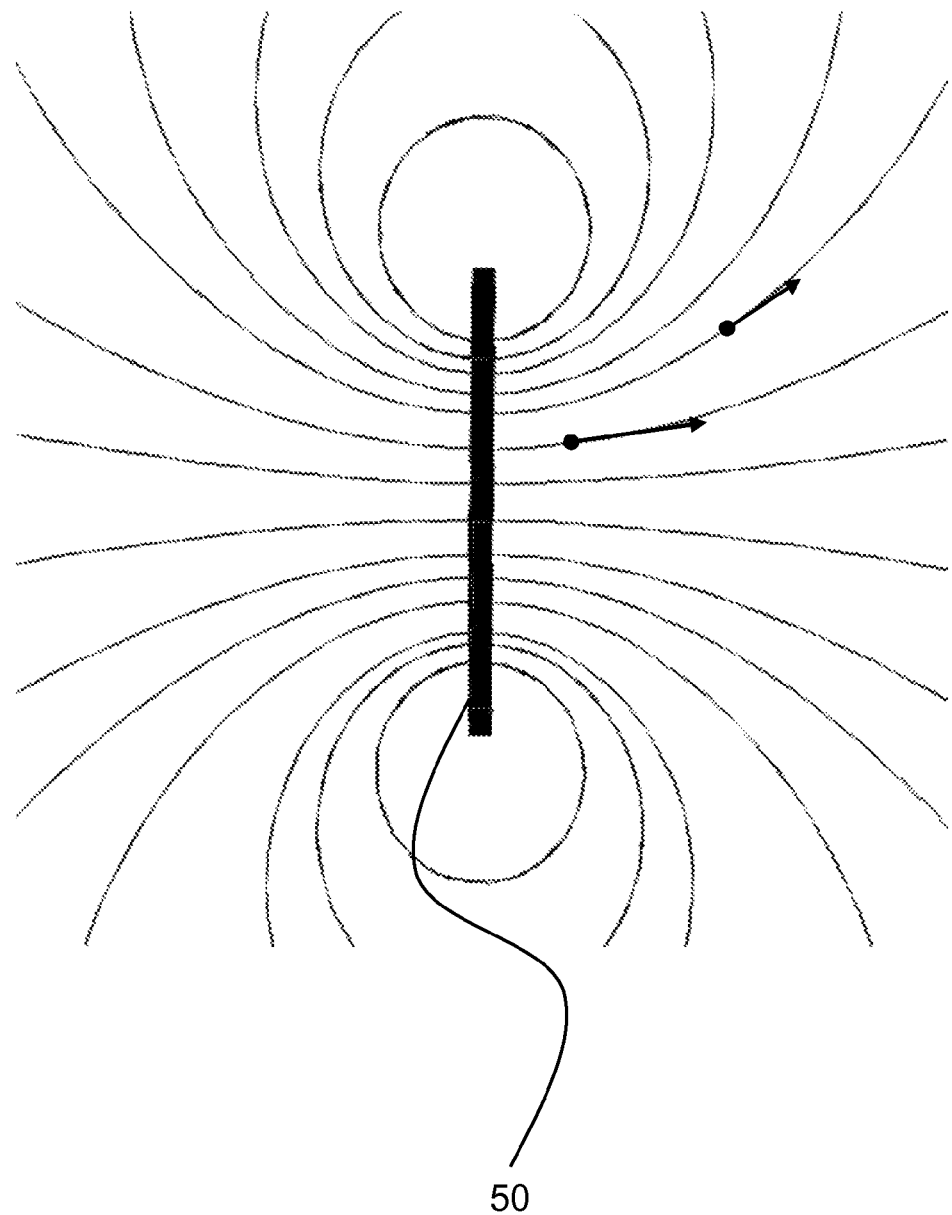
FIG. 4 shows a magnetic field generatable by a coil shown in FIG. 3.

Next, the above partial arrangement will be first discussed theoretically, without the effect of the earth's magnetic field. When position of the imaging sensor (30) in the magnetic field generated by the coil (50) arranged into connection with the radiation source (4) is varied, the three-axis magnetic sensor (M1) arranged into connection with the imaging sensor (30) sees the magnetic field generated by the coil (50) always differently depending on where the magnetic sensor (M1) is positioned in this field. An individual sensor of the three-axis magnetic sensor (M1) whose position in the magnetic field is parallel with the field vector at a point in question does not detect the magnetic field at all, the measurement signal of a sensor located perpendicularly with respect to the field vector equals the field intensity at the point in question, and the signal strength measured by a sensor orientating at an angle to the field vector is cos (ø) of the field intensity at the point in question. When the magnetic field generated by the coil (50) is known, the mutual strengths of partial signals measured by the individual sensors of the three-axis magnetic sensor (M1) define a field vector of specific direction and size which, again, unambiguously defines location of the magnetic sensor in the magnetic field generated by the coil (50). FIG. 4 shows vectors having a specific direction and magnitude (length) which can be determined based on a measurement signal of a magnetic sensor applicable for use in the invention when placed at the locations of the vectors. Then, it is possible based on the measurement signal generated by the magnetic sensor (M1) to e.g. locate the centre of the imaging area of the imaging sensor (30)—at the point of which the magnetic sensor (M1) is preferably located in the sensor as well—on the symmetry axis of the magnetic field generated by the coil (50) at a known distance from the coil (50). When the coil (50) is arranged to the radiation source (4) such that the symmetry axis of the magnetic field generated by it coincides with the centre axis of the x-ray beam generated by the radiation source (4), one is able based on this principle to position the imaging sensor (30) at the centre of the beam generated by the radiation source (4).

In practice, acting according to the above theoretical consideration would not lead into a desired end result as there, the effect of the earth's magnetic field on the measurement signals is not taken into account. In order to be able to determine only the effect of the magnetic field generated by the coil (50) on the measurement signals of the magnetic sensor (M1) arranged into connection with the imaging sensor (30), pulsing of the direct-current supply (PW) of the coil (50) according to a preferred embodiment of the invention is utilised.

Then, the sensor signals can be looked at both in moments of time when they measure only the earth's magnetic field and in moments of time when they also measure the magnetic field generated by the coil (50). When the effect of the earth's magnetic field is eliminated from the result which is obtained when measuring the combined effect of the magnetic field generated by the coil (50) and the earth's magnetic field and when the magnetic field generated by the coil is known, it is possible based on the measurement signals to define a vector which unambiguously defines the location of the imaging sensor (of the magnetic sensor (M1) positioned in the sensor in the magnetic field generated by the coil (50) arranged into connection with the radiation source (4)—and when the location of the coil (50) in the radiation source (4) is known, also its location with respect to the radiation source (4).

Determining location as discussed above can according to one embodiment of the invention be based on a calculation in which the magnetic field generated by the coil (50) arranged into connection with the radiation source is first modelled. The modelling of the magnetic field can be based on concrete measurements of the magnetic field generated by the arrangement within a desired operation sector from the radiation source (4) or it can be implemented by means of a function of relation between location and the direction as well as the intensity of the field. Hence, it is possible to form an error function between this model and the directional vector measured by the magnetic sensor (M1) arranged to the imaging sensor (30). A minimum value with respect to position for this error function can be discovered e.g. by iterating with Newton-Raphson method. This iteration results in the above vector, which unambiguously defines location of the magnetic sensor (M1) in the arrangement. In a preferred embodiment of the invention, this location data can be further transformed to such set of coordinates as determined above, whereby as the end result is a determination of both location of the imaging sensor (30) determined by means of the magnetic field generated by the coil (50) and orientation of the sensor (30) with respect to the beam generated by the radiation source (4) as found out in a way described above.

The transformation of the location data can be implemented e.g. such that, if designating the first cross product of the coordinates obtained from the measurement signals of the magnetic and acceleration sensors vector (Y), and the cross product of this vector (Y) and a vector (A) obtained from the acceleration sensor vector (X), the vectors (X, Y, A) form axes of such orthogonal set of coordinates (M), expressed in the measurement coordinates of the acceleration and magnetic sensors, the x and y axes of which are parallel with the earth's surface, the z axis points downwards and the x axis is parallel with the magnetic field. By defining such a transformation (T), which rotates the vector (Y) to be parallel with a vector (0,1,0) i.e. the y axis, and the vector (X) to be parallel with a vector (1,0,0) i.e. the x axis, a transformation is obtained by means of which it is possible to move between the set of coordinates of the measurement signals of the magnetic and acceleration sensors and the set of coordinates defined by the earth's magnetic and gravitational fields.

Into connection with the collimator plate structure shown in FIG. 3 are preferably arranged means to adjust at least one dimension of the collimator opening, preferably to adjust at least the shape and size of the collimator opening. Also the orientation, location and position of the collimator opening can be arranged adjustable, even thought the orientation and direction of the beam can be adjusted by moving the actual radiation source, too. The functions of the collimator plate structure can be arranged motorised, preferably at least the function of adjusting the size and/or shape of the collimator opening. The motorised function can be arranged automated to adjust the collimator opening according to signals received from the control system of the arrangement, which signals are based on information generated by the control system of the arrangement on the mutual position of the imaging sensor (30) and the radiation source (4) and, further, information on the shape and size of the imaging sensor (30) used in the arrangement. Information relating to the sensor being used can be entered to the arrangement manually or, alternatively, means can be arranged into connection with the sensor (30) by which information relating to the sensor being used (sensor size) is conveyed to the arrangement automatically. Hence, the arrangement can include means to receive information on the imaging sensor (30) which is to be used in imaging, or to receive information on the shape and size of the imaging area of the imaging sensor (30) in question. Such means can comprise a user interface, from which said information is arranged enterable, or the arrangement can include means to receive the information in question via a wired or wireless link directly from the sensor in question. It is also possible to beforehand arrange to the control system information e.g. on various typical characteristics of an opening limited by the collimator structure (4', 40), such as its size, form, location, and position of the opening, whereby the control of motorisation can be arranged to occur based on control signals being based on such preset information and obtained from the control system of the arrangement.

Information corresponding to that being transmittable to the automated collimator can be arranged to be visually presented on a display, whereby the mutual positioning of the sensor and the radiation source can be done manually as guided by the display. On the display, a virtual image of the sensor (30) or the collimator opening limited by the collimator plate structure (40) or equivalent, or both, may be arranged to be presented, or even of the beam in the orientation where it would be with respect to the sensor (30) if the exposure were to be started just at the given moment. Such display is preferably arranged into connection with the radiation source. By this kind of an arrangement it is not only possible to solve the problem that it is practically almost impossible to precisely see in which position the sensor (30) is in a patient's mouth, but it also kind of allows for taking a step further from human sensory aiming to automatic aiming which is based on measurement signals.

The control system can be provided with means to prevent exposure if mutual positioning of the sensor and the radiation source does not fulfil a predetermined accuracy criterion and/or if e.g. a signal is received from the acceleration sensor of the sensor that the sensor is in an acceleration motion greater than the predetermined limit value.

On the other hand and especially in view of a context of hand-held use of the x-ray source, the arrangement can also be implemented so as to automatically initiate an exposure as a response to recognizing that the beam is correctly positioned with respect to the sensor and the sensor is in an acceleration motion slower than the predetermined limit value.

While certain preferable embodiments of the invention have been discussed above, many of the details can be implemented also otherwise without deviating from the basic idea of the invention. For instance, the measurement sensors do not necessarily have to be particularly three-axis, even though using three is already quite adequate. When using magnetic and acceleration sensors, the use of gyro sensors is not necessary, and the different embodiments of the invention can vary, inter alia, within the scope described above in connection with FIG. 3. Substantially, the arrangement includes means arranged into connection with both the imaging sensor and the radiation source to measure their spatial position and to send measurement signals based on these measurements to the control system of the arrangement, which means are preferably at least magnetic sensors. By appropriately choosing sensors and by providing the arrangement with means to generate a magnetic field in a controlled way, it is possible to solve the mutual distance, orientation, angle, location, rotation, or any other equivalent term one wishes to use, of the sensors and, through that, of the components to which they are fixed. All calculations related to such determinations can be arranged as part of the control system of the arrangement and thus, in the arrangement, collimation can be implemented as motorised, automatically, or controlled as based on measurement information generated by the arrangement, not only to aim the beam correctly but also to adjust the size, shape, orientation etc. of the beam optimal for each imaging.

The invention claimed is:

1. An intra-oral x-ray imaging arrangement, which includes as separate structures, first, a radiation source having a collimator structure limiting an x-ray beam for generating the beam used in imaging and for aiming the x-ray beam toward an object to be imaged, second, an imaging sensor arranged positionable within a patient's mouth, and a system controlling the imaging arrangement, wherein the imaging arrangement includes a signal generating means arranged in connection with both the imaging sensor and the radiation source which signal generating means includes a means to measure a spatial position of the imaging sensor and the radiation source and a means to send measurement signals based on these spatial position measurements, and wherein the system controlling the imaging arrangement includes a means to determine information on a relative spatial position between the imaging sensor and the radiation source or of a component arranged to the radiation source based on said measurement signals, and wherein said collimator structure includes a structure which enables adjusting a collimator opening limited by the collimator structure for at least one of the following: its size, its shape, its location, its position, which structure for adjusting the collimator opening is motorized or powered by other electric means and its control is based on control signals received from the system controlling the imaging arrangement.

2. An imaging arrangement according to claim 1, wherein said collimator structure includes a collimator tube within which said structure for adjusting the collimator opening is arranged.

3. An imaging arrangement according to claim 2, wherein said structure for adjusting the collimator opening is arranged within said collimator tube at a distance from an opening of the collimator tube from where the beam generated by the radiation source is directed at the object.

4. An imaging arrangement according to claim 1, wherein said adjusting of the collimator opening is based on at least one of the following:
   i) said means which are arranged to send to the system controlling the imaging arrangement measurement signals including a position of at least one component pertaining to the arrangement, and the adjusting of the collimator opening takes place on the basis of the control signals which are based on said measurement signals received from the system controlling the imaging arrangement;
   ii) means to receive information on the imaging sensor which is to be used in imaging or information on the shape and size of an image area of said imaging sensor, and the adjusting of the collimator opening is based on the control signals which are based on said information received by the system controlling the imaging arrangement;
   iii) the system controlling the imaging arrangement is arranged to comprise preset information to set at least one of the following: the size, the shape, the location, the position of the opening limited by the collimator structure, and the adjusting of the collimator opening is based on control signals which are based on said preset information from the system controlling the imaging arrangement.

5. An imaging arrangement according to claim 4, wherein said means to receive information related to the imaging sensor comprises a user interface from which said information is arranged to be entered, or means to receive the information via a wired or wireless link directly from the associated sensor.

6. An imaging arrangement according to claim 1, wherein said signal generating means include an at least three-axis magnetic sensor in connection with the imaging sensor.

7. An imaging arrangement according to claim 1, wherein said signal generating means include an at least three-axis magnetic sensor in connection with the radiation source.

8. An imaging arrangement according to claim 1, wherein said signal generating means includes a three-axis acceleration sensor in connection with the imaging sensor and a three-axis acceleration sensor in connection with the radiation source.

9. An imaging arrangement according to claim 1, wherein said signal generating means includes an at least three-axis acceleration sensor and an at least three-axis magnetic sensor in connection with the imaging sensor and an at least three-axis acceleration sensor and an at least three-axis magnetic sensor in connection with the radiation source, wherein the system controlling the arrangement is provided with a means to calculate on the basis of measurement signals obtained from the three-axis sensors a relative spatial orientation between the imaging sensor and the radiation source or between the imaging sensor and a component associated with the radiation source.

10. An imaging arrangement according to claim 9, wherein in connection with said collimator structure is arranged a coil having a functional connection with a power supply, and wherein the system controlling the imaging arrangement includes a means to controllably generate a direct-current magnetic field by means of said coil, wherein the system controlling the imaging arrangement is provided with a means to calculate on the basis of measurement signals obtained from the associated magnetic sensor, which measurement signals have been measured both in situations in which said coil is directed by means of said power supply to induce a magnetic field and in situations in which said coil does not induce a magnetic field, at least one of the following:
   i) a distance between the imaging sensor and the radiation source or some component arranged to the radiation source;
   ii) a direction or a distance, or both, at which the imaging sensor is located with respect to a centre axis of the beam generated by the radiation source;
   iii) a directional vector defining a location of the associated magnetic sensor in the magnetic field generated by the coil.

11. An imaging arrangement according to claim 10, wherein said means to calculate the relative spatial position between the imaging sensor and the radiation source and to calculate said directional vector includes an algorithm recorded on a data storage medium which is arranged to solve at least one or all of the following:
  i) first, based on the measurement signals of the acceleration sensors arranged into connection with the imaging sensor and the radiation source, second, based on the measurement signals of the magnetic sensors arranged into connection with the imaging sensor and the radiation source measuring the earth's magnetic field, solve a relative tilt angle of the imaging sensor and the radiation source, or some component arranged to the radiation source, in one set of coordinates;
  ii) first, based on the measurement signals of the acceleration sensors arranged into connection with the imaging sensor and the radiation source, second, based on the measurement signals of the magnetic sensors arranged into connection with the imaging sensor and the radiation source measuring the earth's magnetic field, solve a mutual orientation of the imaging sensor and the radiation source, or some component arranged to the radiation source, in one set of coordinates;
  iii) based on the measurement signal of the magnetic sensor arranged into connection with the imaging sensor of the difference of, first, the measurement signal of the magnetic field generated by the coil and, second, of the measurement signal measuring the earth's magnetic field, solve a distance between the imaging sensor and the radiation source, or some component arranged to the radiation source;
  iv) based on the measurement signal of the magnetic sensor arranged into connection with the imaging sensor of the difference of, first, the measurement of the magnetic field generated by the coil and, second, of the measurement signal measuring the earth's magnetic field, solve a direction or a distance, or both of these, in which the imaging sensor is located with respect to a symmetry axis of the magnetic field generated by the coil;
  v) based on the measurement signal of the magnetic sensor arranged into connection with the imaging sensor of the difference of, first, the measurement of the magnetic field generated by the coil and, second, of the measurement signal measuring the earth's magnetic field, solve a direction vector defining location of the associated magnetic sensor in the magnetic field generated by the coil.

12. An imaging arrangement according to claim 11, wherein said coil is placed into connection with the collimator structure such that a symmetry axis of the magnetic field generated by the coil coincides with a centre ray of the x-ray beam generated by the radiation source and limited by the collimator structure of the radiation source.

13. An imaging arrangement according to claim 10, wherein said coil is placed into connection with the collimator structure such that a symmetry axis of the magnetic field generated by the coil coincides with a centre ray of the x-ray beam generated by the radiation source and limited by the collimator structure of the radiation source.

14. An imaging arrangement according to claim 10, wherein the arrangement includes a display or another means for transmitting information, which is arranged into connection with the radiation source or physically separate from the arrangement, and wherein the system controlling the imaging arrangement generates mutual location information between the imaging sensor and the radiation source in a graphical or other form based on said directional vector to be displayed on the associated display or another means for transmitting information.

15. An imaging arrangement according to claim 10, wherein said control signals are at least partially based on said directional vector.

16. An imaging arrangement according to claim 1, wherein said signal generating means include an at least three-axis magnetic sensor arranged into connection with the imaging sensor, individual sensors of which are located substantially close to each other and/or substantially in the middle of an image area of the imaging sensor.

17. An imaging arrangement according to claim 1, wherein in connection with at least one of the imaging sensor and the radiation source of the arrangement is arranged a gyro sensor which is configured to send position information to the system controlling the imaging arrangement, which system is arranged to correct as a function of time the position information obtained from the gyro sensor based on a measurement signal obtained from at least one other position measuring sensor.

18. An imaging arrangement according to claim 1, wherein the arrangement includes a display or another means for transmitting information, which is arranged into connection with the radiation source or physically separate from the arrangement, and wherein the system controlling the imaging arrangement generates position information related to the relative position between the imaging sensor and the radiation source in a graphical or other form, to be displayed on the associated display or another means for transmitting information.

19. An imaging arrangement according to claim 18, wherein the system controlling the imaging arrangement is provided with means to show on the display a virtual image of the sensor or of the collimator opening limited by the collimator structure, or both, or of the x-ray beam in an orientation in which it would be at a given time with respect to the sensor, if exposure were to be started at said given time.

20. An imaging arrangement according to claim 1, wherein said control signals are arranged at least partially to be based on information calculated based on said measurement signals of the relative spatial position between the imaging sensor and the radiation source.

21. An imaging arrangement according claim 20, wherein in functional connection with the system controlling the imaging arrangement are arranged means to transmit information to the system controlling the imaging arrangement on dimensions of an image area of the imaging sensor used in the arrangement, and said control signals for the motorising are arranged to be based on information calculated based on measurement signals received from said signal generating means which information comprises at least one of the following: a relative tilt angle between the imaging sensor and the radiation source; a relative rotation between the imaging sensor and the radiation source; a distance between the imaging sensor and the radiation source.

22. An imaging arrangement according to claim 1, wherein said adjustment of the opening of the collimator structure limiting the x-ray beam is arranged motorised and control of the motorising is based on control signals received from the system controlling the imaging arrangement, which control signals are arranged to comprise preset information for setting at least one of the following: the size, the shape, the location, the position of the opening limited by the collimator structure.

23. An imaging arrangement according to claim 1, wherein a means has been arranged to the system controlling the imaging arrangement to prevent exposure in case the relative spatial position of the imaging sensor and the radiation source does not fulfill a predefined accuracy criterion and/or if a signal is received from the signal generating means of the imaging sensor that the imaging sensor is in an acceleration motion greater than a predetermined limit value.

24. An imaging arrangement according to claim 1, wherein a means has been arranged to the system controlling the imaging arrangement to initiate an exposure as a response to recognizing that the beam produced by the radiation source is correctly positioned with respect to the imaging sensor and the imaging sensor is in an acceleration motion slower than a predetermined limit value.

* * * * *